US011000323B2

(12) United States Patent
Stamp et al.

(10) Patent No.: US 11,000,323 B2
(45) Date of Patent: May 11, 2021

(54) CLAW FOOT BONE PLATE AND PLATE INSERTER SYSTEM WITH FIXED AND ACTIVE COMPRESSION, AND METHOD FOR ITS USE

(71) Applicant: ORTHO SOLUTIONS HOLDINGS LIMITED, Littleton, CO (US)

(72) Inventors: Kevin Stamp, Sheffield (GB); Dustin Ducharme, Littleton, CO (US); Alister Maclure, Chelmsford (GB)

(73) Assignee: ORTHO SOLUTIONS HOLDINGS LIMITED, Littleton, CO (US)

( * ) Notice: Subject to any disclaimer, the term of this patent is extended or adjusted under 35 U.S.C. 154(b) by 135 days.

(21) Appl. No.: 16/429,604

(22) Filed: Jun. 3, 2019

(65) Prior Publication Data

US 2019/0365438 A1    Dec. 5, 2019

Related U.S. Application Data

(60) Provisional application No. 62/679,228, filed on Jun. 1, 2018.

(51) Int. Cl.
*A61B 17/80* (2006.01)
*A61B 17/064* (2006.01)
(Continued)

(52) U.S. Cl.
CPC ...... *A61B 17/8061* (2013.01); *A61B 17/0642* (2013.01); *A61B 17/8004* (2013.01);
(Continued)

(58) Field of Classification Search
CPC ........ A61B 17/0642; A61B 2017/0645; A61B 17/068; A61B 17/80; A61B 17/8004; A61B 17/8019; A61B 17/8061; A61B 17/808; A61B 17/809; A61B 17/8872; A61F 2/4611
See application file for complete search history.

(56) References Cited

U.S. PATENT DOCUMENTS 5,695,524 A    12/1997    Kelley et al.
5,715,987 A    2/1998    Kelley et al.
(Continued)

FOREIGN PATENT DOCUMENTS

AU    2013206096 B2    1/2014
CA       2817333 A1    12/2013
(Continued)

*Primary Examiner* — Larry E Waggle, Jr.
(74) *Attorney, Agent, or Firm* — Hudak, Shunk & Farine Co. LPA

(57) ABSTRACT

The invention is a super elastic bone plate and inserter. The bone plate has a plate section with openings for screws at fixed or variable angles, an optional compression slot, and a pronged section (i.e. the claw foot), which is generally transverse to the long axis of the plate for insertion, and after deployment returns to an angle of less than 90° to impart compression at a bone/bone interface, e.g. to cause fusion between bone segments. The inserter, which has a first leg with a frictional fit holding block for the plate and a second leg with a holding and activation mechanism for the super elastic pronged section. The invention also relates to a method of bone fusion using the plate system.

14 Claims, 8 Drawing Sheets

(51) Int. Cl.
*A61B 17/88* (2006.01)
*A61B 17/84* (2006.01)

(52) U.S. Cl.
CPC ........ *A61B 17/808* (2013.01); *A61B 17/8872* (2013.01); *A61B 17/8033* (2013.01); *A61B 17/8057* (2013.01); *A61B 17/846* (2013.01); *A61B 2017/0645* (2013.01)

(56) References Cited

U.S. PATENT DOCUMENTS

| | | |
|---|---|---|
| 6,059,787 A | 5/2000 | Allen |
| 6,083,242 A | 7/2000 | Cook |
| 6,348,054 B1 | 2/2002 | Allen |
| 6,755,831 B2 * | 6/2004 | Putnam .............. A61B 17/1728 606/102 |
| 6,783,531 B2 | 8/2004 | Allen |
| 7,572,276 B2 * | 8/2009 | Lim .................. A61B 17/7083 606/246 |
| 8,235,995 B2 | 8/2012 | Focht et al. |
| 8,584,853 B2 | 11/2013 | Knight et al. |
| 8,596,514 B2 | 12/2013 | Miller et al. |
| 8,628,533 B2 * | 1/2014 | Graham ............... A61B 17/809 606/70 |
| 8,721,646 B2 | 5/2014 | Fox |
| 8,808,294 B2 | 8/2014 | Fox et al. |
| 8,821,508 B2 * | 9/2014 | Medoff .................. A61B 17/92 606/99 |
| 9,017,331 B2 | 4/2015 | Fox |
| 9,095,338 B2 | 8/2015 | Taylor et al. |
| 9,101,349 B2 | 8/2015 | Knight et al. |
| 9,101,421 B2 * | 8/2015 | Blacklidge ......... A61B 17/8004 |
| 9,204,932 B2 | 12/2015 | Knight et al. |
| D748,258 S | 1/2016 | Gledel |
| 9,433,452 B2 * | 9/2016 | Weiner ................ A61B 17/809 |
| 10,004,603 B2 * | 6/2018 | Appenzeller ............. A61F 2/28 |
| 10,792,081 B2 * | 10/2020 | Weiner ................ A61B 17/809 |
| 2002/0173793 A1 | 11/2002 | Allen |
| 2007/0233113 A1 * | 10/2007 | Kaelblein ............ A61B 17/809 606/71 |
| 2010/0063506 A1 | 3/2010 | Fox et al. |
| 2012/0228355 A1 | 9/2012 | Combrowski et al. |
| 2013/0026206 A1 | 1/2013 | Fox |
| 2013/0041406 A1 | 2/2013 | Bear et al. |
| 2013/0206815 A1 | 8/2013 | Fox |
| 2013/0231667 A1 | 9/2013 | Taylor et al. |
| 2013/0331839 A1 | 12/2013 | Hester et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0034702 A1 | 2/2014 | Miller et al. |
| 2014/0097228 A1 | 4/2014 | Taylor et al. |
| 2014/0277516 A1 | 9/2014 | Miller et al. |
| 2016/0235460 A1 | 8/2016 | Wahl |
| 2017/0100163 A1 | 4/2017 | Palmer et al. |
| 2017/0231625 A1 | 8/2017 | Handie |
| 2017/0281157 A1 | 10/2017 | Hartdegen et al. |
| 2018/0289366 A1 | 10/2018 | Morgan et al. |
| 2018/0353172 A1 | 12/2018 | Hartdegen et al. |
| 2019/0046182 A1 | 2/2019 | Krumme |
| 2019/0231349 A1 | 8/2019 | Wahl et al. |
| 2019/0282231 A1 | 9/2019 | Vasta |
| 2020/0000464 A1 | 1/2020 | Gaston et al. |
| 2020/0008807 A1 | 1/2020 | Hollis |
| 2020/0038076 A1 | 2/2020 | Amis et al. |
| 2020/0100820 A1 | 4/2020 | Hollis et al. |

FOREIGN PATENT DOCUMENTS

| | | |
|---|---|---|
| CN | 103479409 A | 1/2014 |
| CN | 102579116 B | 12/2015 |
| CN | 103732155 B | 9/2017 |
| DE | 102012100086 A1 | 8/2012 |
| EP | 1179994 B1 | 6/2006 |
| EP | 1772107 A1 | 11/2007 |
| EP | 2474271 A2 | 11/2012 |
| EP | 2736421 B1 | 6/2014 |
| EP | 2671517 B1 | 3/2017 |
| EP | 2741683 B1 | 7/2019 |
| JP | 2013255796 A | 12/2013 |
| WO | 2013055824 A1 | 4/2013 |
| WO | 2013130978 A2 | 9/2013 |
| WO | 2014058954 A2 | 4/2014 |
| WO | 2014120955 A1 | 8/2014 |

\* cited by examiner

CLAW FOOT BONE PLATE AND PLATE INSERTER SYSTEM WITH FIXED AND ACTIVE COMPRESSION, AND METHOD FOR ITS USE

FIELD OF THE INVENTION

The invention comprises a room temperature super elastic Nitinol bone plate and inserter for its use intended for bone fixation in the surgical management of fractures and bone reconstruction, for example for use in the foot and hand. The invention also relates to a method of use for the inserter and the plate of the present invention.

BACKGROUND OF THE INVENTION

Over 1.8 million orthopedic trauma fixation procedures were performed in the US in 2016, and the market is expected to reach over $4 billion by 2025. The fastest growing part of the market is the staple fixation segment, which is also expected to remain the fastest growing through to 2025. The primary drivers for growth are reportedly a reduced operating time as compared to screws, and plates. Plates are generally metallic frameworks with a broad outline and thickness to support bone segments fixed to the framework or "plate" by screws, pins, or nails that extend through the plate. The plates are wider, thicker and longer than alternative fixation means that overlay the bone surface in the form of staples or mesh. Thus, plates provide additional material to allow for specialized screw interaction, like locking or polyaxial screws and an outline and fixation angles that provides bridging for fusion and even reduction of typical bone break patterns. They generally have a bone-facing surface that corresponds to the bone segments and a top surface which corresponds to the topography of the bottom surface separated by a constant through thickness, at least for a portion of the plate. Bone staples generally have a long thin rectangular central bridging member which joins a pair or more of opposing legs that extend downward from the bridge member.

While the state of the art has advanced the use of bone staples, there remain cases in which an implant that presents the advantages of a plate along with the dynamic compressive and holding abilities of a staple, or in this case, a multiply pronged plate, can be of great advantage in ease of use and in a mechanical advantage. The particular invention provides these advantages in the pronged plate, and in the system for its use. In particular, the inserter is capable of single handed use, and is able to deform the prongs of the plate to cause the super elastic deformation, while permitting easy and reliable deployment of the claw portion of the plate in bone.

The design can be used for single use in which case cost will be a greater consideration, drawing in materials and manufacturing methods that meet economic requirements while presenting a design that is sufficiently strong to reliably accomplish the job. This means that the inserter provides that the claw foot portion of the plate can be deformed, inserted into pre-drilled pilot holes and tamped into position across a bone divide, all in a design that is quick, reliable, and easy to use, and advantageously single-handedly and the plate portion can be used to provide the support and scaffolding that is often desired in a plate, along with a unique combination of active and fixed compression fixation which offers multiple advantages.

SUMMARY OF THE INVENTION

The invention provides an inserter for a super elastic compressive bone plate having a first plate end and a second claw-foot end. The bone plate has a plate section having a curved bone facing surface and outline to allow multiple screw holes and guide wire slots and which is shaped to extend along an axis which extends along the length of a bone or bone segment. At an opposite end, the plate has a pronged section (a plurality of pointed, tapered angled extensions, i.e. the prongs, which collectively form the claw foot), which is generally transverse to the axis of the plate for insertion, and after deployment returns to an angle of less than 90° to impart compression at a bone/bone interface, e.g. to cause fusion between bone segments. The plate section includes openings for fixation members, typically screws or pegs including fixed angle or locking screws, and optionally a compression slot through the plate, and preferably parallel to the plate axis, to drive further compression in the direction of the claw foot end. Preferably there are at least two prongs and at least two fixation members through the plate, so that there are at least four points of fixation, two on either side of the joint.

In a preferable configuration for the bone plate a first end of the plate has a typical plate construction, which includes an elongate plate member including openings for fixation including an outline optionally configured to accommodate lobes for non-linear fixator attachment. The plate member has a bottom or bone facing surface which typically is curved to accommodate the shape of the bone which it opposes, and spaced from that by a through thickness, which is typically relatively uniform, the member also includes a top surface, which faces out away from the bone and has a shape which corresponds to the shape of the bone-facing surface. On the opposite end, the plate includes a claw foot member, which has one or more prongs, and preferably two or even three or four prong members that extend at least in one state, in a direction transverse to an axis along the main portion of the plate (i.e. that backbone). The claw foot further includes a slot between the prongs so that the plate can be held on one side on an inserter leg with a holding mechanism that is captured in the slot, and between the prongs.

The plate member further has an outline to accommodate openings for fasteners, such as screws placed to best capture bone as designed for a particular application. Thus, the plate member may include one or more lobes that are rounded to provide collars for associated fixation holes so as to sufficient material to capture the screw head and optionally means to interface with the screw, such as locking threads or rounded opening for variable locking hemispherical screw heads. The plate portion is also illustrated with a compression slot, aligned with the axis of the screw or the direction which compression is optimally applied and which may include a sliding component to provide compression, or a ramp which interacts with the screw head to generate compression as the screw is screwed into the underlying bone.

The claw foot portion of the plate provides a substantially L-shaped portion, i.e. a plate having a transverse plate member and one or more, and preferably two, downwardly extending prongs or legs, which can be biased into a parallel "activated position" for insertion into the bone, and then released into a compressive configuration.

The invention also relates to an inserter, which has a first leg that scissors relative to a second leg and the first leg. The inserter holds the plate during implantation, and the first leg includes a block that is sized to hold the plate in a central location, such as a friction fit with a slot along the backbone of the plate, while the second leg includes a mechanism to hold the plate prongs in a transverse position relative to the spine of the plate. In a first embodiment, the plate holding mechanism includes two opposed cylindrical post members secured to the lower leg in a transverse direction so as to engage the inside of the plate prongs and causes them to expand to a transverse position relative to the plate axis for insertion. In a further embodiment, the holding mechanism is a pair of retractable holders, such as bearing members or ball plungers held in a socket, and which will retract back into the socket when a trigger driven force is applied to them. In both instances, the lower leg of the inserter includes a holder block that easily fits inside the plate slot and is sized and shaped so that the second leg of the inserter can be disengaged from the claw foot after the prongs are inserted into an initial position in the bone. In the first embodiment the disengagement is caused by sliding the holder leg further to the inside of the claw and rotating the leg to enable the post member to thread through the claw slot for disengagement.

After disengagement, the prongs of the claw member can revert to a second position which is at a smaller angle than 90° to cause the pronged members of the claw end to apply a compressive force to the bone. At this point, screws are inserted through the plate, and the plate end is also fixed. Initial locations on the bone can be set following a reduction of the bones by using k-wires which can extend through screw holes in the plate, or optionally, k-wire holes can also be provided or alternatively, an olive wire can be used through a wire slot. In addition, temporary compression can be applied across the joint through the use of an external compression clamp.

In accordance with the invention, the plate can be mounted on the inserter, and following a reduction, the claw-end can be inserted at a first position while it is on the inserter. The inserted can be removed, and the claw foot end can be tamped into position on the bones. Then, the plate portion can be fixed on the bone using fixed angle or variable angle locking screws, for example, and applying any additional compression, for example, through the activation of the claw foot end, or by using a mechanical compression slot in the plate.

The claw foot is fabricated in a closed (converging legs) shape and is mechanically deformed or "activated" by the inserter during use to induce the super elastic shape memory properties in the claw foot so as to compress bone segments and facilitate osteosynthesis in use. The claw foot is held on the inserter on rounded expanders and the inserter has a mechanism to spread the expanders which opens the legs so that the super elastic properties are induced and the legs are spread into transverse positions for implantation. The mechanism uses a scissoring assembly which draws apart a pair of pivoting leg members. The bone plate is configured to accommodate fixation procedures in the forefoot, midfoot, rearfoot and hand, and the sterilizable or disposable inserter allows implantation of the plate in bone in a surgical procedure so as to apply a compressive force across a division of bone segments so as to facilitate bone fusion between the segments.

Prior to the deployment of the plate in the bone, the inserter includes a holding mechanism which secures the plate so that it is constrained on the bottom side at the corners of the plate member where the prongs join the plate member and on the top side in a more central portion of the plate member. The plate member is also secured against a second leg of the inserter in a slot on the plate member.

The rounded expander holders of the inserter retain the claw of the plate in a non-preloaded/non-energized position but interface with the plate in the proximal corners. This captures the plate securely on the inserter and permits the activation of the plate for deployment. In a first embodiment, the holding members are fixed cylindrical posts that are rotated for disengagement of the slot, and in a further embodiment, the inserter includes a trigger activated retraction mechanism and a pair of floating ball bearings (which can any appropriate shape, include spherical, or ovoid, or egg-shaped) rather than the fixed post members that hold and activate the prongs of the plate into a deploy position in which the prongs are perpendicular to the spine of the plate for implantation into bone.

The inserter can be advantageously pre-assembled (i.e. prior to surgery) with plate in a non-activated state (i.e. in which the prongs converge toward the plate, at an angle of from 60° to 88°, and preferably at an angle from 70° to 85° relative to an axis along the plate member). The inserter further includes an easy to use mechanism for "activating" the staple by deforming the prongs to a transverse position and initiating the super elastic properties of the plate material. The inserter can also include a mechanical stop for the prongs, so that it is inhibited from plastically deforming the staple legs and the super elastic properties are mitigated by entering that threshold.

DETAILED DESCRIPTION OF THE INVENTION

Figure 1:
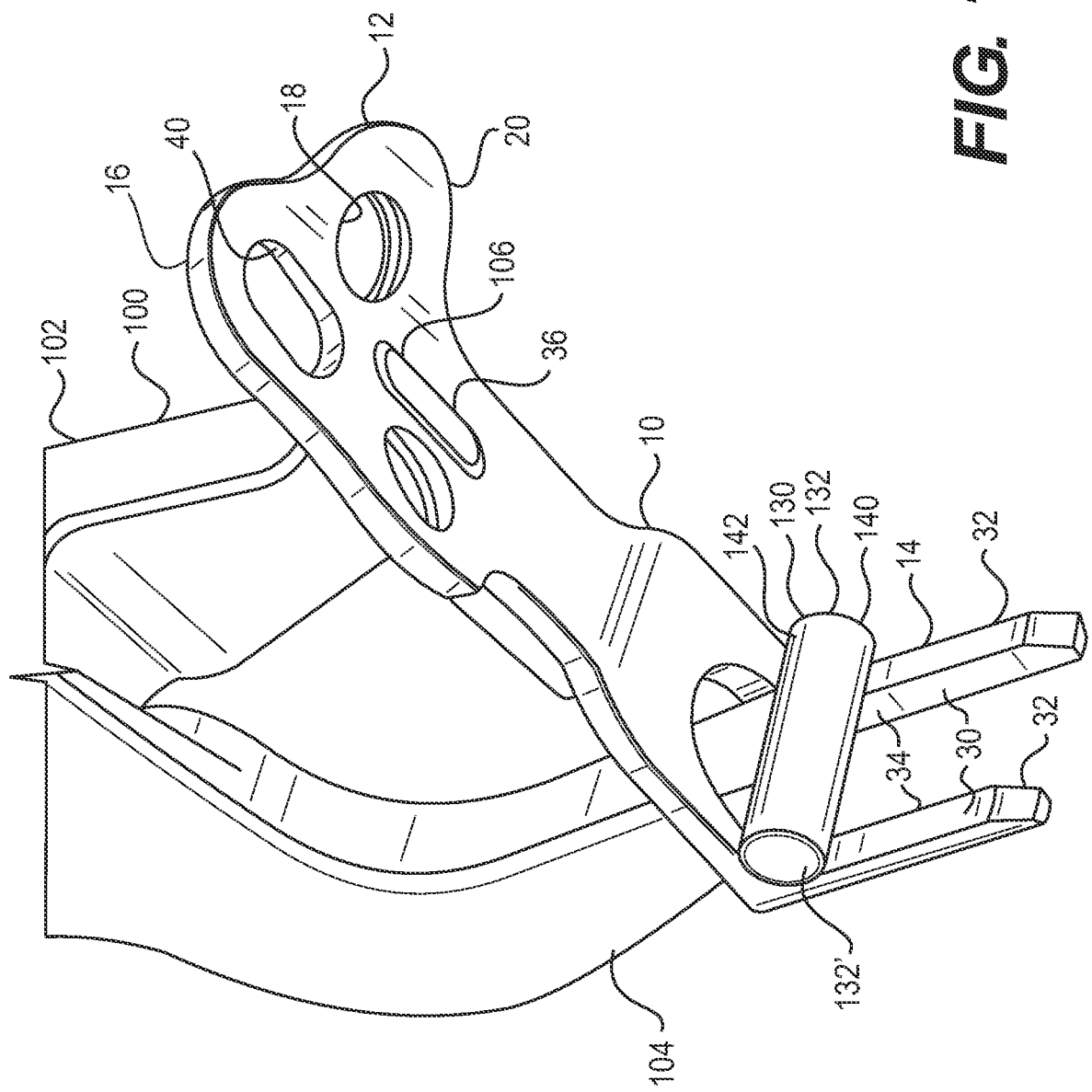
FIG. 1 shows a bottom side view of the plate and inserter with a staple in accordance with the present invention.
Figure 2:
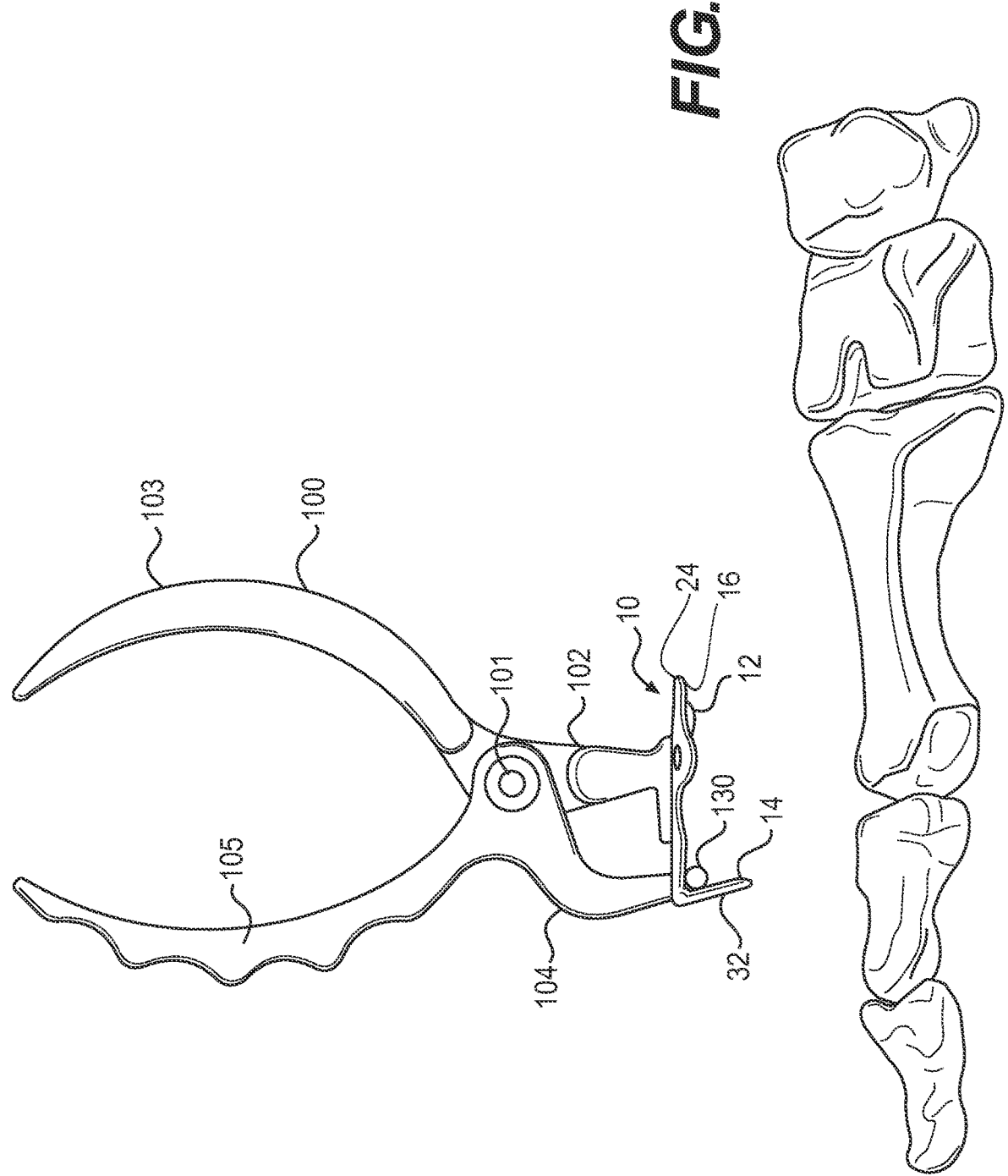
FIG. 2 shows a top view of the plate and inserter of FIG. 1 in position relative to a foot.
Figure 3:
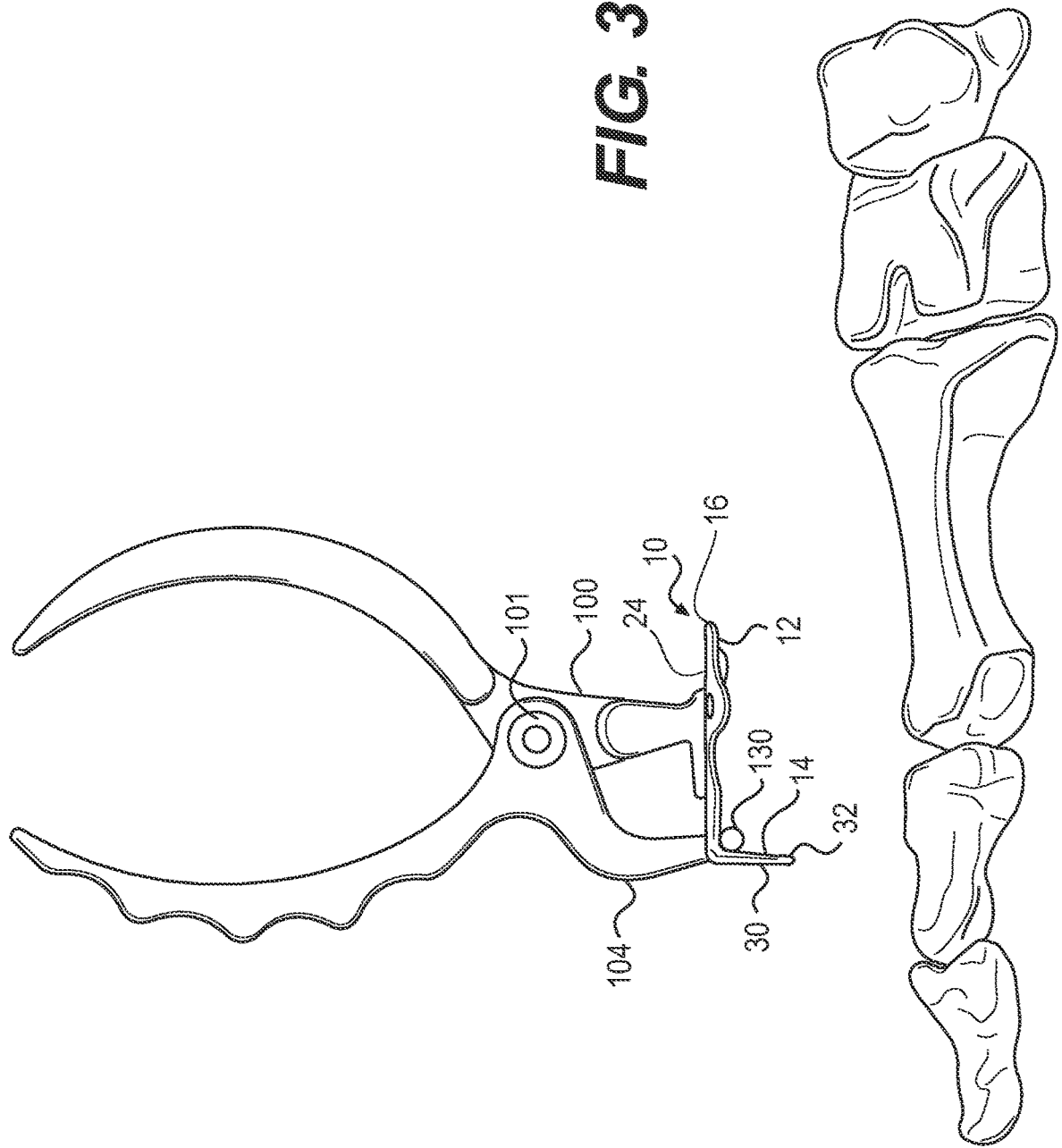
FIG. 3 shows a side view of the plate and inserter where the plate is activated for insertion into the staple leg holes.
Figure 4:
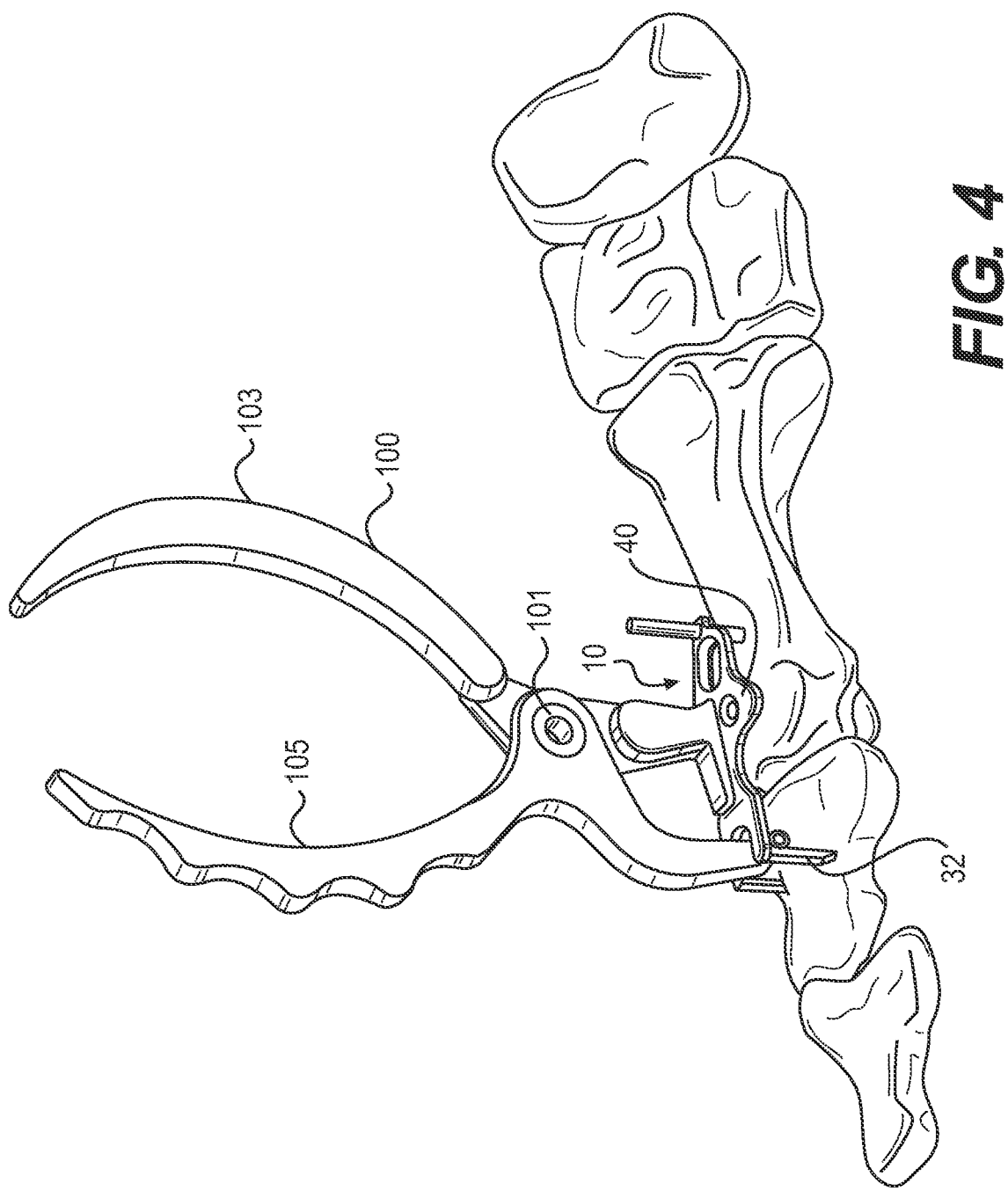
FIG. 4 is a top side view of the plate and inserter with the plate activated by the inserter.

The invention provides an inserter for a super elastic compressive bone plate 10 having a first plate end 12 and a second claw-foot end 14. In a preferable configuration for the bone plate 10 a first end 12 of the plate has a typical plate construction, which includes an elongate plate member 16 including openings 18 for fixation including an outline optionally configured to accommodate lobes or rounded extensions which are contiguous with the surfaces of the plate 10 for non-linear fixator attachment. The plate member 12 has a bottom or bone facing surface 22 which typically is curved to accommodate the shape of the bone which it opposes, and spaced from that by a through thickness, which is typically relatively uniform, the member also includes a top surface 24, which faces out away from the bone and has a shape which corresponds to the shape of the bone-facing surface. On the opposite end 14, the plate includes an insertion end, and preferably at least two prong members, (i.e. from 2-4, and more preferably 2) that extend at least in one state, in a direction transverse to an axis along the main portion of the plate (i.e. that backbone). The claw foot 30 further includes a slot 34 between the prongs so that the plate 10 can be held on one side on an inserter 100 having a leg 102 that is captured in the slot 34, and between the prongs 32. The plate member 12 further includes a holding slot 36 that has a friction fit with a block member 106 on the inserter 100.

The plate member 12 further has an outline to accommodate openings 18 for fasteners (not shown), such as screws placed to best capture bone as designed for a particular application. Thus, the plate member 12 may include one or more lobes 20 that are rounded to provide sufficient material to capture the screw head and optionally means to interface with the screw, such as locking threads or rounded opening for variable locking hemispherical screw heads. The plate portion 12 is also illustrated with a compression slot 40, which may include a sliding component to provide compression, or a ramp which interacts with the screw head to generate compression as a compression screw is screwed into the underlying bone.

The claw foot portion 14 of the plate 10 provides a substantially L-shaped portion, i.e. a plate having a transverse plate member and downwardly extending prongs or legs 32, which can be biased into a parallel "activated position" for insertion into the bone, and then released into a compressive configuration. The inserter 100 can be advantageously pre-assembled (i.e. prior to surgery) with plate 10 in a non-activated state (i.e. in which the prongs converge toward the plate, at an angle of from 60° to 88°, and preferably at an angle from 70° to 85° relative to an axis along the plate member). The inserter 100 further includes an easy to use mechanism for "activating" the staple by deforming the prongs 32 to a transverse position and initiating the super elastic properties of the plate material.

Figure 5:
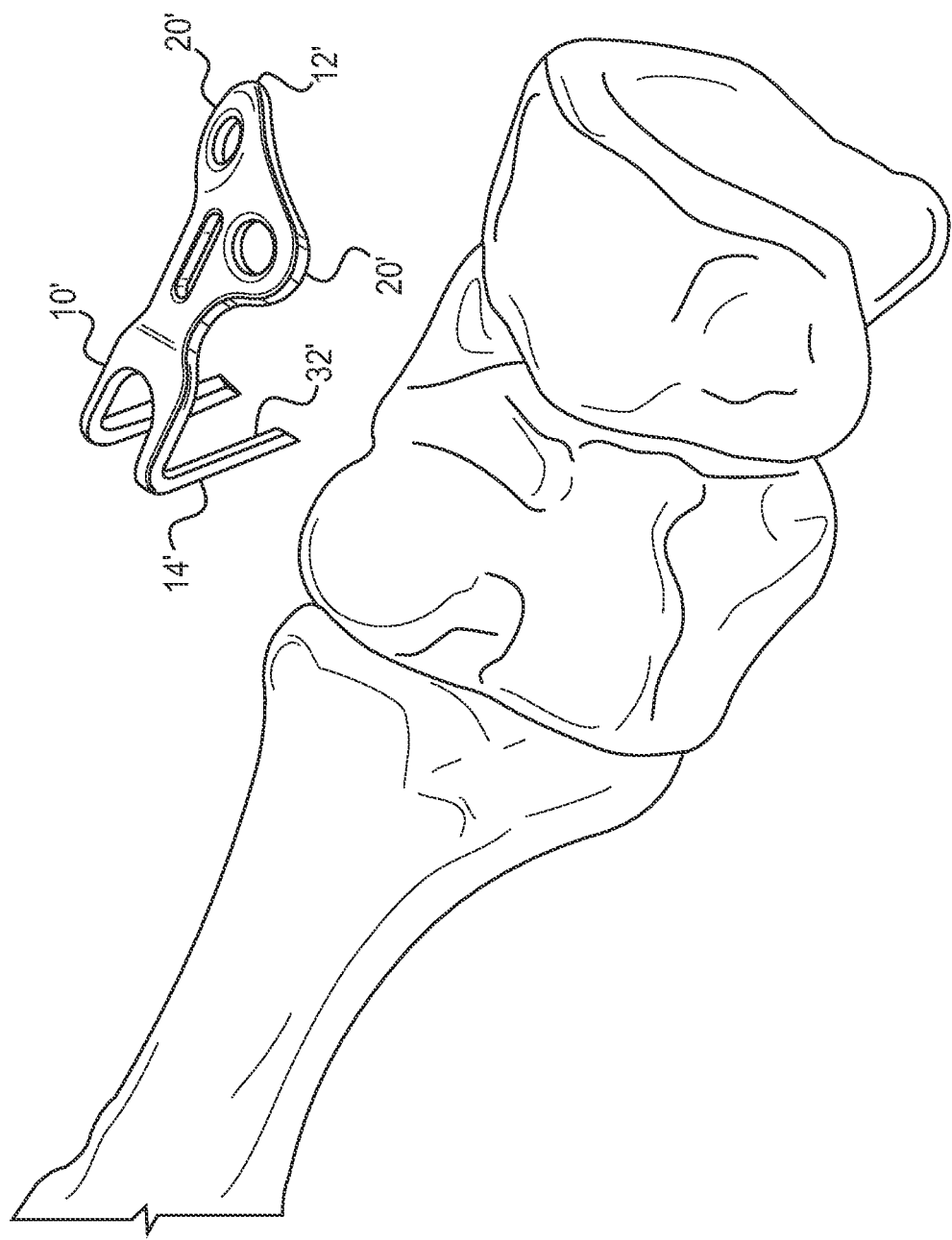
FIG. 5 is a top side view of a second embodiment of the claw-foot plate of the present invention situation above the bones of a foot.
Figure 6:
FIG. 6 is a view of the plate of FIG. 5 with the clawfoot plate of the present invention in position in the bones of the foot.
Figure 7:
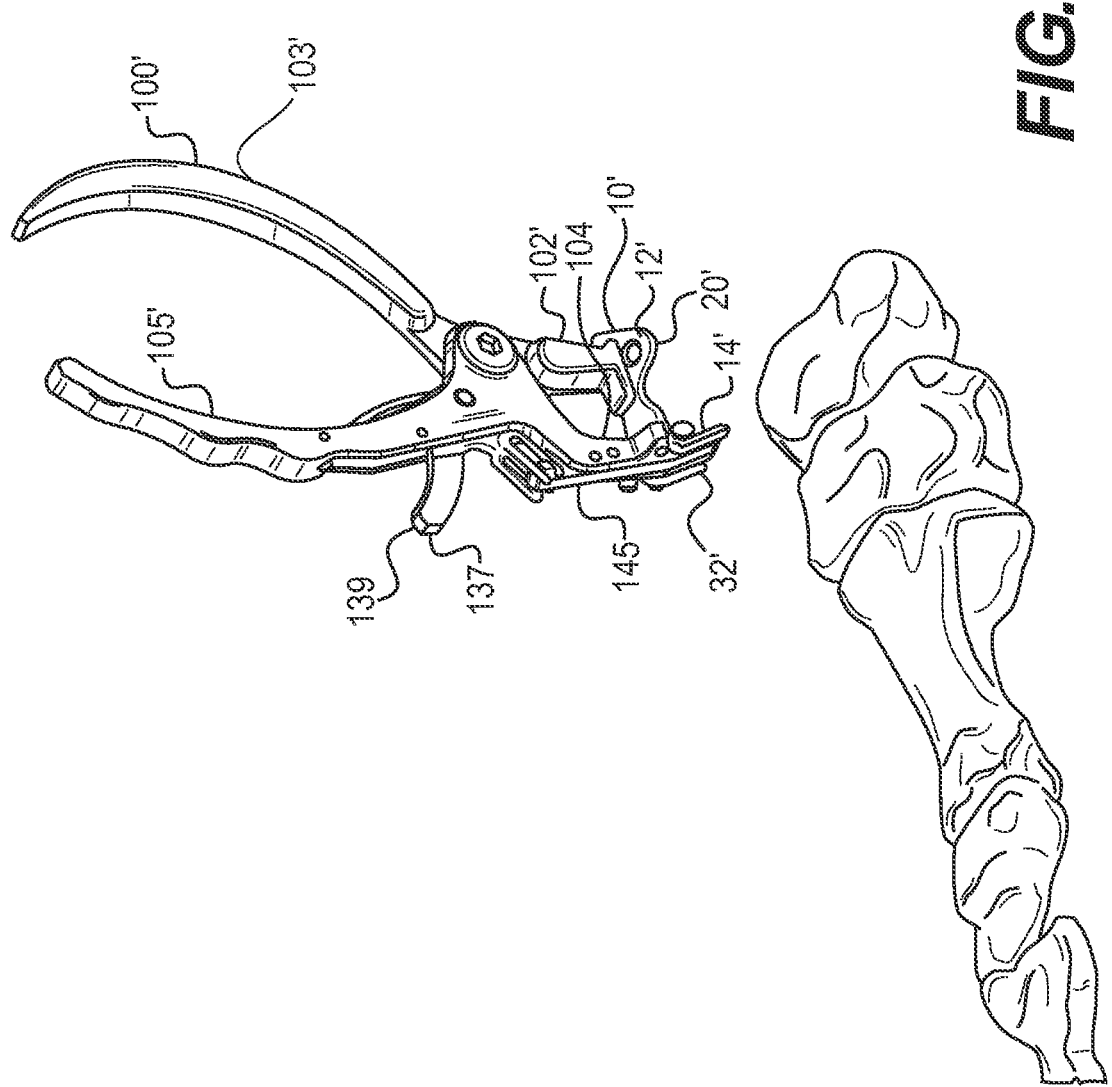
FIG. 7 is a top side view of a second embodiment of the inserted of the present invention holding the plate of FIG. 5 in position above a foot.

A second embodiment of the plate of the present invention is illustrated in FIGS. 5-7. This plate 10' has a plate member 12' which is modified in the outline of the plate, and which includes two lobed portions 20' and which lacks the compression slot 40 of the first embodiment. On the other end, the plate includes a claw-foot portion 14' with downwardly extending legs 32'.

The inserter 100 has a pair of scissoring legs 102, 104, which pivot relative to each other about a pivot mechanism 101 and where the first first leg terminates in a block member 106 which is configured to engage and be securely held within a holding slot 36 in the plate 10 such as by a frictional fit including a wedging interface. The legs 102, 104 each extend outward from the pivot point 101 into handle members 103, 105 respectively for manipulation of the plate 10 during implantation. The pivoting mechanism includes a lock so that the position of the inserter legs and thereby the position of the plate on the inserter can be fixed for application to the bone site.

The second leg 104 includes a mechanism 130 for holding and activating the prongs 32 of the plate 10. This mechanism 130 includes rounded engagement members 132 that extend transverse to the long direction of the leg 104. The engagement members 132 engage the underside of the prongs 32 and plate member 12 so as to enable the inserter to apply a force to the prongs to cause them to be moved into a perpendicular position for insertion into pre-drilled holes in the bone.

Prior to the deployment of the plate 10 in the bone, a first leg 102 of the inserter 100 holds the plate 10 so that it is constrained on the bottom side 22 at the corners of the plate member where the prongs 32 join the plate member 12 and on the top side 24 in a more central portion of the plate member 12. The plate member 12 is also secured against a second leg 104 of the inserter in a holding slot 36 on the plate member 12.

A rounded expander engagement member 132, 132' of the inserter 100 retains the claw foot 30 of the plate 10 in a non-preloaded/non-energized position but interfaces with the plate in the proximal corners. This captures the plate securely on the inserter and permits activation of the plate 10 for deployment.

In a first embodiment, the holding mechanism 130 includes a set of posts 140 as the engagement members 132. Preferably, the posts have a rounded outer surface 142 that engage the prong/plate connection. As the legs 102, 104 are spread apart, this surface 142 applies a force to the prongs and to the plate through the holding slot 36 which activates the prong into the transverse position to allow the plate prongs to be tamped using the inserter into a first position. Thereafter, the holding block 106 on the first leg 102 is disengaged from the plate and the inserter is rotated down and back away from the plate member to clear the first leg from the plate 10. Then, the inserter can be rotated about the long axis of the second leg 104 to disengage the second leg 104 from the slot 34 between the prongs 32 of the plate 10.

Figure 8:
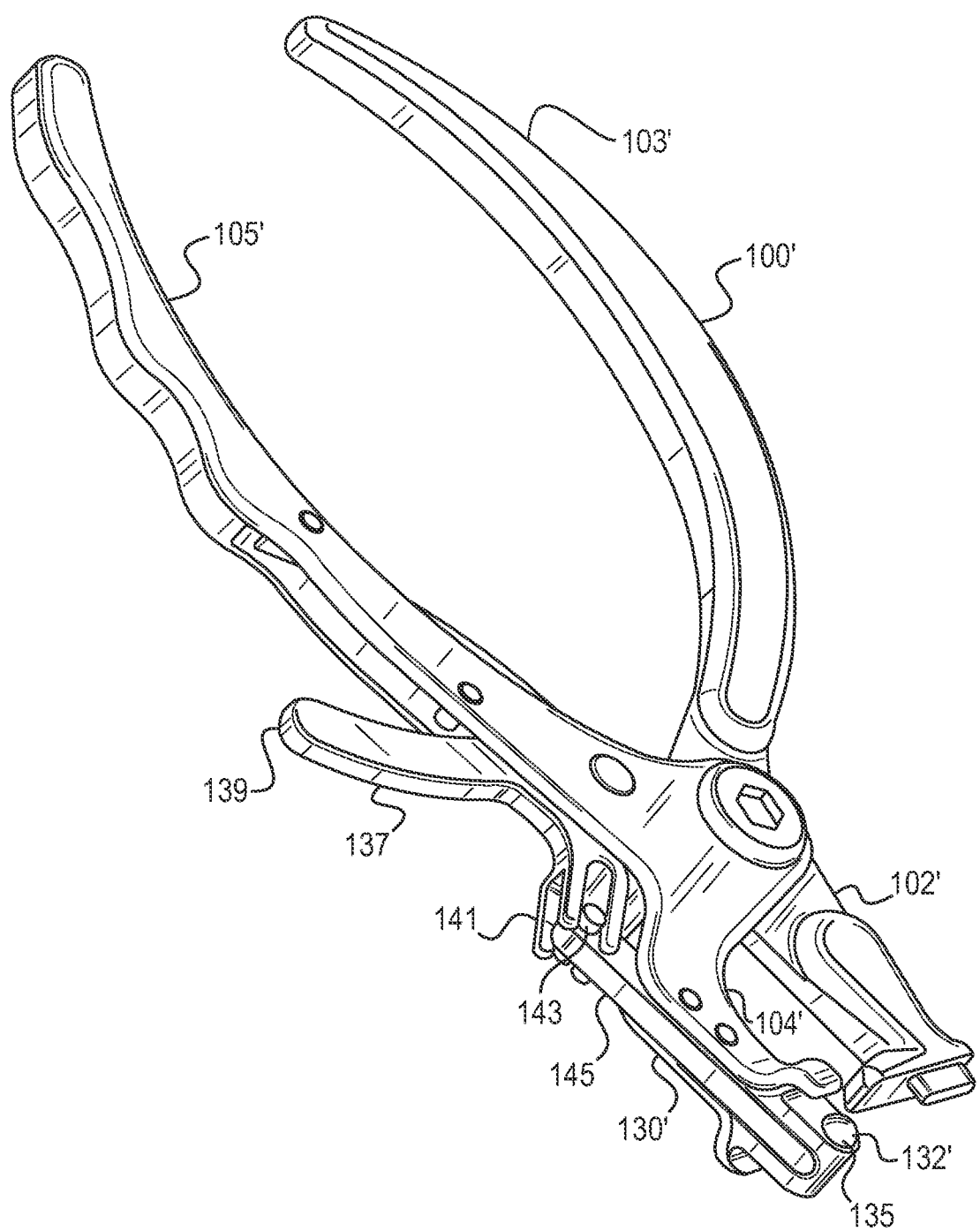
FIG. 8 shows a bottom side perspective of the inserter of FIG. 7.

In a second embodiment of the inserter 100', shown in FIGS. 7 and 8, also includes a pair of scissoring legs 102', 104' joined to handle members 103', 105', and the holding mechanism 130' includes rounded engagement members 132' that float in a socket 135 in the second leg 104'. In this case, the engagement members are preferably bearings, including, for example, ball bearings, and are press fit into the socket which retains them by means of a collar connection. The bearings are urged outward by means of a trigger mechanism 137, that has an activation trigger 139, joined to a fork 141 which engages a boss 143 on a lever arm 145. The lever arm terminates in a cooperation member that urges the engagement members outward in the deployed mode and allows them to retract in the disengagement mode.

The operation of the inserter 100 for implantation of the claw foot plate 10 is described as follows:

The plate 10 of the invention is loaded onto the inserter 100 for implantation by engaging the holding slot 36 with the block member and with the rounded engagement mechanism in the slot 34 between the prongs 32 of the claw foot portion of the plate 10. The legs 102, 104 of the inserter are urged apart to cause the plate to be activated for deployment.

After the selected bone segments are prepared such as by preparing opposing cone osteotomy segments placed together by k-wires and drilling appropriate pilot holes for the prong members, the plate is placed over the k-wire and into a position for engaging the prong pilot holes.

The prongs of the plate are tamped into an initial position sufficiently above the bone surface in order that the inserter can be disengaged, and in this position, the holding mechanism is disengaged from the plate.

The plate is urged into a closer contact with the bone segments, and the screws are inserted through the screw holes into engagement with the plate holes and the bone, and optionally, a compression screw is inserted through the compression slot in the plate.

In the final position, the prongs return to the pre-activated angle and the plate applies fixed compression to one bone segment by means of the locking or fixed angle screws, and active compression across the bone/bone interface by means of the super elastic quality of the prongs.

The plate inserter of the present invention is suitable for manufacture via injection molding, but could also be fabricated from other manufacturing techniques such as, but not limited to, machined, 3-d printed or stamped components. The inserter can be fabricated from plastic or metal materials, or a combination of both.

The plate and inserter are configured to accommodate different fixation procedures in the forefoot, midfoot, rearfoot and hand, and the inserter allows implantation of the staple in bone in a surgical procedure so as to apply a compressive force across a division of bone segments for fracture and osteotomy fixation of the hand and foot, including joint arthrodesis and to stabilize and dynamically compress bone fragments to facilitate osteosynthesis.

What is claimed is:

1. An orthopedic plate and inserter system, comprising a super elastic plate and inserter wherein the super elastic plate has a bone long axis with a bone facing surface defining a curve along the axis in a direction other than a direction of the long axis along a first end and an opposed surface, and along the long axis first end having a plate member with an outline with a plurality of lobes and having screw holes in the lobes and a second end having at least two prongs which have an activated position at a transverse angle to the axis, and the inserter has a first leg and a second leg and the first leg pivots relative to the second leg, and the first leg includes a holding mechanism that engages the bone facing surface of the at least two prongs to cause the prongs to move into the activated position and the second leg has a block that engages a slot in the plate member.

2. An orthopedic plate and inserter system as set forth in claim 1 wherein the plate second end has a claw foot member.

3. An orthopedic plate and inserter system as set forth in claim 2, wherein the screw holes are for non-linear fixator attachment to a bone segment.

4. An orthopedic plate and inserter system as set forth in claim 2, wherein the claw foot member has the at least two prongs that extend at least in one state, in a direction transverse to the axis along a main portion of the plate.

5. An orthopedic plate and inserter system as set forth in claim 4, further comprising a slot between the two prongs so that the plate is configured for engagement of the plate inserter.

6. An orthopedic plate and inserter system as set forth in claim 5, wherein the claw foot member is held on the first leg on the slot between the two prongs.

7. An orthopedic plate and inserter system as set forth in claim 2, wherein the plate bone facing surface is curved to accommodate a shape of a bone segment, and the plate bone facing surface is spaced from the opposed surface by a uniform through thickness for at least a portion of the first end.

8. An orthopedic plate and inserter system as set forth in claim 1, wherein the outline has two or three lobes.

9. An orthopedic plate and inserter system as set forth in claim 1, wherein the slot has a friction fit with the block.

10. An orthopedic plate and inserter system as set forth in claim 1, wherein the holding mechanism includes a pair of rounded engagement members.

11. An orthopedic plate and inserter system as set forth in claim 10, wherein the first leg includes a socket which captures two rounded engagement members which are bearing members that are activated by a trigger to allow the engagement members to retract into the socket.

12. An orthopedic plate and inserter system as set forth in claim 1, wherein the first and second leg can be locked into a fixed position relative to each other.

13. A method of fusing bone, comprising:
preparing at least two bone segments for fusion and drilling two pilot holes for a first and a second prong of a super elastic plate;
loading a super elastic plate on an inserter which has a first leg and a second leg, wherein the super elastic plate has a bone long axis with a bone facing surface defining a curve along the axis in a direction other than a direction of the axis along a first end and an opposed surface and along the axis first end having a plate member having screw holes and a second end having the two prongs which have an activated position at a transverse angle to the axis, and wherein the first leg pivots relative to the second leg, and the first leg includes a holding mechanism that engages the bone facing surface of the at least two prongs to cause the prongs to move into the activated position and the second leg has a block that engages a slot in the plate member,
using the inserter to move the prongs into the activated position and to insert the prongs into the pilot holes;
disengaging the inserter from the plate; and
fixing the plate to the bone segments by inserting screws through the screw holes.

14. A method of fusing bones as set forth in claim 13, wherein the plate is pre-loaded on the inserter to hold the prongs in the activated position prior to surgery.

* * * * *